(12) United States Patent
Park et al.

(10) Patent No.: US 10,254,348 B2
(45) Date of Patent: Apr. 9, 2019

(54) METHOD AND APPARATUS FOR DETECTING ABNORMAL STATE OF BATTERY

(71) Applicant: SAMSUNG ELECTRONICS CO., LTD, Suwon-si (KR)

(72) Inventors: Jeonghyun Park, Seoul (KR); Jaemo Sung, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 704 days.

(21) Appl. No.: 14/589,294

(22) Filed: Jan. 5, 2015

(65) Prior Publication Data

US 2016/0018345 A1 Jan. 21, 2016

(30) Foreign Application Priority Data

Jul. 21, 2014 (KR) ........................ 10-2014-0091966

(51) Int. Cl.
  *G01N 25/72* (2006.01)
  *G01R 31/36* (2019.01)
  *G01R 31/367* (2019.01)
  *G01R 31/382* (2019.01)

(52) U.S. Cl.
  CPC ....... *G01R 31/3648* (2013.01); *G01R 31/367* (2019.01); *G01R 31/382* (2019.01); *G01N 25/72* (2013.01)

(58) Field of Classification Search
  USPC .......................................................... 702/63
  See application file for complete search history.

(56) References Cited

U.S. PATENT DOCUMENTS

| 8,269,463 | B2 | 9/2012 | Nakashima et al. | |
| 8,446,127 | B2* | 5/2013 | Yazami | H01M 10/443 320/132 |
| 2003/0129457 | A1* | 7/2003 | Kawai | G01R 31/3658 429/7 |
| 2009/0155674 | A1 | 6/2009 | Ikeuchi et al. | |
| 2010/0076714 | A1* | 3/2010 | Discenzo | H02N 2/181 702/104 |
| 2010/0188050 | A1 | 7/2010 | Asakura et al. | |
| 2012/0169290 | A1* | 7/2012 | Nakashima | H01M 10/44 320/134 |
| 2013/0322488 | A1* | 12/2013 | Yazami | G01N 27/27 374/142 |

(Continued)

FOREIGN PATENT DOCUMENTS

| CN | 103325070 A | 9/2013 |
| JP | 4215171 B2 | 1/2009 |

(Continued)

*Primary Examiner* — Paul D Lee
(74) *Attorney, Agent, or Firm* — NSIP Law

(57) ABSTRACT

A method and apparatus for detecting an abnormal state of a battery are provided. An entropy calculator is configured to calculate an information entropy based on battery estimation information and battery measurement information. The battery estimation information corresponds to an output required from the battery, and the battery measurement information is collected from the battery. A battery abnormality determiner is configured to determine whether the battery is in the abnormal state based on the information entropy.

25 Claims, 10 Drawing Sheets

(56) References Cited

U.S. PATENT DOCUMENTS

| | | | | | |
|---|---|---|---|---|---|
| 2013/0338871 | A1* | 12/2013 | Kubo | ............... | G01R 31/3606 |
| | | | | | 701/29.2 |
| 2014/0354233 | A1* | 12/2014 | Yazami | ............. | G01R 31/3679 |
| | | | | | 320/127 |
| 2015/0377977 | A1* | 12/2015 | Yazami | ............. | G01R 31/3651 |
| | | | | | 324/426 |
| 2016/0207415 | A1* | 7/2016 | Sato | .................... | B60L 3/0046 |

FOREIGN PATENT DOCUMENTS

| | | |
|---|---|---|
| JP | 2010-60406 A | 3/2010 |
| JP | 2011-113688 A | 6/2011 |
| JP | 2012-26749 A | 2/2012 |
| JP | 2012-42457 A | 3/2012 |
| JP | 5326973 B2 | 10/2013 |
| KR | 10-0814883 B1 | 3/2008 |

\* cited by examiner

METHOD AND APPARATUS FOR DETECTING ABNORMAL STATE OF BATTERY

CROSS-REFERENCE TO RELATED APPLICATION(S)

This application claims the benefit under 35 USC § 119(a) of Korean Patent Application No. 10-2014-0091966, filed on Jul. 21, 2014, in the Korean Intellectual Property Office, the entire disclosure of which is incorporated herein by reference for all purposes.

BACKGROUND

1. Field

The following description relates to a method and apparatus to detect an abnormal state of a battery.

2. Description of Related Art

Use of apparatuses equipped with batteries has rapidly increased. Batteries are used in apparatuses in which mobility is an important factor. For example, batteries are mounted in smartphones, notebook computers, or electric vehicles (EVs). The above apparatuses require an increasingly higher capacity and, accordingly, a demand for increased capacity of batteries mounted in mobile apparatuses is increasing.

When a capacity of a battery mounted in an apparatus increases, problems may increase with the use of such battery, such as battery exploding. For example, in a hearing aid apparatus placed within an ear canal of a person (for example, a smartphone), a risk of the battery exploding, albeit being a small explosion, may create a life-threatening injury to the person. In another example, when a battery in an EV explodes during vehicle operation, life threatening human injuries and/or material damages may occur. Further, an enterprise brand image may be greatly damaged. Additionally, in an energy storage system, human, material damages, and/or anxiety fatal to society may occur.

Accordingly, there is a desire for technologies to develop a stable and reliable battery, while providing increased capacity.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided an apparatus to detect an abnormal state of a battery, the apparatus including an entropy calculator configured to calculate an information entropy based on battery estimation information and battery measurement information, wherein the battery estimation information corresponds to an output required from the battery, and the battery measurement information is collected from the battery; and a battery abnormality determiner configured to determine whether the battery is in the abnormal state based on the information entropy.

The apparatus may also include a battery information collector configured to collect the battery measurement information; a usage information collector configured to collect usage information of a usage history of an electronic apparatus including the battery; and an estimator configured to acquire the battery estimation information from the usage information.

The estimator may be configured to transform the usage information to a power corresponding to the output, and to calculate a voltage corresponding to the power.

The apparatus may also include an estimator configured to extract the battery estimation information from an electrical model of the battery.

The apparatus may also include a storage configured to store a result of a comparison between the battery estimation information and the battery measurement information during a time window of a predetermined length.

The entropy calculator may be configured to calculate the information entropy based on a result of a comparison between the battery estimation information and the battery measurement information.

The entropy calculator may be configured to calculate a difference between the battery estimation information and the battery measurement information, to calculate a probability that the difference occurs, and to calculate the information entropy from the probability.

The battery abnormality determiner may be configured to determine that the battery is in the abnormal state in response to a value of the information entropy being greater than a threshold.

The battery abnormality determiner may be configured to determine that the battery is in the abnormal state in response to an interval, in which a value of the information entropy is greater than a threshold, being detected to be equal to or greater than an interval.

In accordance with an embodiment, there is provided a method to detect an abnormal state of a battery, the method includes calculating an information entropy based on battery estimation information and battery measurement information, wherein the battery estimation information corresponds to an output required from the battery, and the battery measurement information is collected from the battery; and determining whether the battery is in the abnormal state based on the information entropy.

The method may also include collecting the battery measurement information from the battery; collecting usage information associated with a usage history of an electronic apparatus including the battery; and estimating the battery estimation information from the usage information.

The estimating may include transforming the usage information to a power corresponding to the output and calculating a voltage corresponding to the power.

The calculating may include storing a result of a comparison between the battery estimation information and the battery measurement information during a time window of a predetermined length to calculate the information entropy.

The calculating may include calculating the information entropy based on a result of a comparison between the battery estimation information and the battery measurement information.

The calculating may include calculating a difference between the battery estimation information and the battery measurement information; calculating a probability of the difference from occurring; and calculating the information entropy from the probability.

The determining may include determining that the battery is in the abnormal state in response to a value of the information entropy being greater than a threshold.

In accordance with an embodiment, there is provided a method to detect an abnormal state of a battery, the method including collecting battery measurement information from the battery; acquiring battery estimation information from an output required from the battery; and comparing the battery measurement information and the battery estimation information to determine whether the battery is in an abnormal state.

The acquiring may include collecting usage information associated with a usage history of an electronic apparatus including the battery; and transforming the usage information to a power corresponding to the output and calculating a voltage corresponding to the power.

The method may also include determining that the battery is in the abnormal state in response to a difference between the battery estimation information and the battery measurement information being greater than a threshold.

In accordance with an embodiment, there is provided a non-transitory computer readable recording medium storing a program to cause a computer to implement the method described above.

In accordance with an embodiment, there is provided a battery abnormality detection apparatus, including a battery information collector configured to collect battery measurement information from a battery; a usage information collector configured to collect usage information associated with a usage history of an electronic apparatus including the battery and transform the usage information to a power corresponding to an output required from the battery; an estimator configured to acquire battery estimation information from the usage information, or from an estimated voltage based on the power; an entropy calculator configured to calculate an information entropy based on the battery estimation information and the battery measurement information; and a battery abnormality determiner configured to determine, based on the information entropy, whether the battery is in the abnormal state.

The apparatus may also include a storage configured to store a difference between the battery estimation information and the battery measurement information during a time window of a predetermined length in which the entropy calculator calculates the information entropy; and a notifier configured to notify a current state of the battery as the abnormal state, in response to the battery abnormality determiner determining that the battery is in the abnormal state.

The battery measurement information may include at least one of a measured voltage signal, a measured current signal, and a measured temperature signal of the battery.

The power may be calculated from the output and raw data corresponding to the usage information during a time window of a predetermined length, and the time window is a temporal length of information set to compute the information entropy.

The battery estimation information may include the power and the estimated voltage, an estimated current, or an estimated temperature estimated from the usage information, and information corresponding to a required output from the battery.

The estimator may be further configured to receive the power, receive a voltage signal collected at the battery information collector, and apply the received voltage signal to a current and an internal resistance of the battery to acquire the estimated voltage.

Other features and aspects will be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which.

Figure 1:
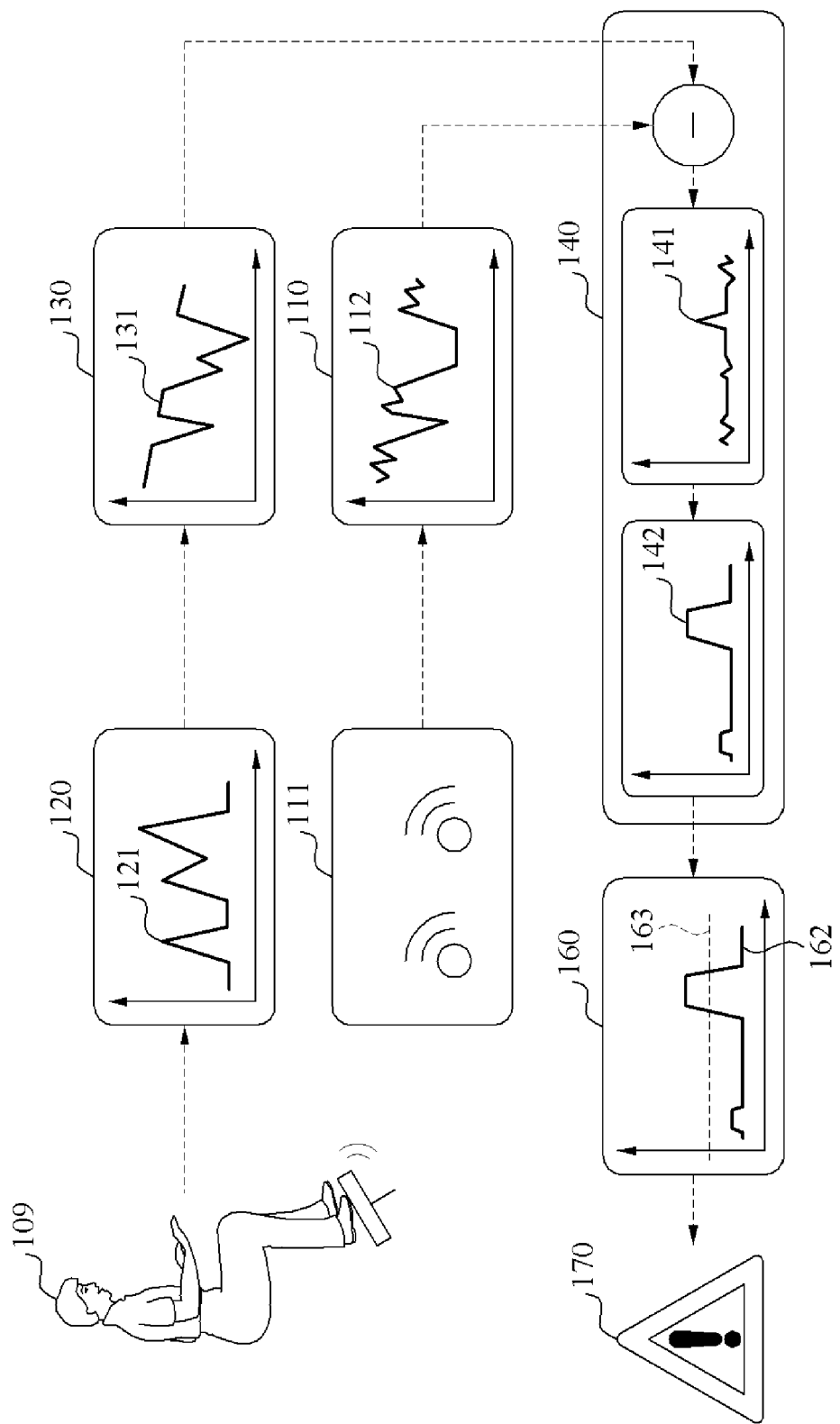
FIG. 1 is a diagram illustrating an example of an apparatus and a process thereof to detect an abnormal state of a battery based on usage information, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, an abnormal state of a battery includes, for example, all states in which the battery does not normally operate. An abnormal state of a battery includes, for example, an internal short circuit, an external short circuit, penetration, or a thermal exposure. When a battery is excessively discharged or charged, when the battery is continuously exposed to an environment outside the recommended operating temperature, or when a strong external electrical or mechanical shock is applied to the battery, the battery enters an abnormal state. When an abnormality or a phenomenon occurs in the battery, or example blow of gas, thermal runaway, or an explosion in the battery, the battery may not operate despite a remaining energy capacity in the battery.

In an illustrative example, to detect an abnormal state of a battery in an electronic apparatus, a protection device, for example, a protection circuit module (PCM), or a battery management system (BMS), in the electronic apparatus is connected to a battery system. Accordingly, the electronic apparatus may be protected. When a value of a voltage or a current measured by the protection device is equal to or greater than a predetermined value, the protection device disconnects the battery from the electronic apparatus, to protect the electronic apparatus. The electronic apparatus is, for example, a smartphone, or an electric vehicle (EV).

The protection device blocks the battery from the rest of the hardware in the electronic apparatus. In one example, the battery is blocked immediately before an occurrence of an abnormality that allows the battery to be unavailable. Despite blocking of the battery, the electronic apparatus may be damaged, the battery may still be damaged, or a battery accident may occur, due to the abnormality in the battery. Additionally, because only an abnormal phenomenon that is to cause a serious accident may be detected, an abnormal state in which the electronic apparatus or the battery may be damaged may not be detected.

In one example, an abnormal state of a battery may be detected as follows. In a moment in which a voltage drop of a battery exceeds a threshold, the battery is determined to be in the abnormal state. In another example, when a change ratio of a voltage to a capacity is less than a threshold, the battery is determined to be in the abnormal state. In still another example, based on a distribution of values of a variable representing a state of the battery during a predetermined period of time, the abnormal state of the battery may be detected.

However, in the above examples to detect the abnormal state of the battery, the battery may be erroneously determined to be in the abnormal state, upon an occurrence of a voltage drop caused by a reduction in a life of the battery, a voltage drop caused by an increase in power consumption of the battery when the battery is exposed to an extreme external environment (for example, a low external temperature), and a voltage drop caused by an external stimulus (for example, a high output required during use of the battery). Rather than correctly detecting a malfunction of the battery, a voltage drop of a battery may occur due to an external stimulus or an external environment to which an electronic apparatus equipped with the battery is exposed, instead of due to battery malfunctions. Accordingly, in the above examples, a voltage drop of a battery may not be determined to be caused by the abnormal state of the battery.

In accordance with an embodiment, an electronic apparatus is described including an electrical structural product equipped with a battery, and may be, for example, an EV, a smartphone, a cellular phone, a notebook personal computer (PC), or a tablet PC.

FIG. 1 illustrates an example of an apparatus and a process thereof to detect an abnormal state of a battery based on usage information, in accordance with an embodiment.

Referring to FIG. 1, an apparatus to detect an abnormal state of a battery, hereinafter referred to as a battery abnormality detection apparatus, detects the abnormal state, based on usage information associated with a usage history of the battery. The usage history indicates past and current usage of a battery in an electronic apparatus in response to a user's past and current operation. The usage history includes, for example, a control history associated with all operations the user applied to the electronic apparatus before a power charged to and discharged from a battery is determined. In an example, a usage history of an electrical vehicle (EV) includes an intensity measured when a user presses an accelerator pedal, a time period during which the accelerator pedal is pressed, an amount of pressure measured when the user presses a brake pedal, a time duration in which the brake pedal is pressed, and the like. In another example, a usage history of a smartphone includes a time period to turn on a screen of the smartphone, a time duration in which an application is executed, a touch history of a touch screen, and the like.

The usage information is information on use of a battery in an electronic apparatus. The usage information is associated with an ideal amount of power required to be output from a battery, and is used to acquire battery estimation information. The usage information includes load information on a load applied to a battery in an electronic apparatus based on a usage history (for example, a user's operation). For example, usage information of an EV includes, but is not limited to, a revolutions per minute (RPM) and a torque determined by a degree to which a user presses an accelerator pedal. Accordingly, the usage information includes a usage history. The load information includes information associated with a power required to be output from a battery.

The battery estimation information includes all information corresponding to an ideal output required to be output from a battery, and includes, for example, an estimated voltage, an estimated current, an estimated temperature, or an estimated capacity of a battery. The battery estimation information will be further described below.

In FIG. 1, battery measurement information collected at a sensor 111 is all information, such as battery measurement information, measured from the battery, and includes, for example, a measured voltage, a measured current, a measured temperature, or a measured capacity of the battery. Additionally, the battery measurement information includes a change due to an abnormal state of the battery, and a change due to a usage history of an electronic apparatus. The changes may include a change in a voltage, a current, or an internal resistance of the battery.

When the battery measurement information the sensor 111 collects is used without a change, a change in the battery measurement information is not classified as a change due to the abnormal state or a change due to the usage history. In one illustrative example, a range of change due to an abnormal state is set to be greater than a range of change due to the usage history. Thus, the abnormal state of the battery is not detected when the change of the battery measurement information is within the range of the change due to the usage history.

In FIG. 1, a usage information collector 120 in the battery abnormality detection apparatus collects usage information associated with a usage history of a user 109. In an example, the usage information collector 120 transfer the usage information to an estimator 130 without a change. In another example, the usage information collector 120 transforms the usage information to an output 121 required to be output from the battery, and transfers the output 121 to the estimator 130. The output 121 corresponds to a power P required to be output from the battery.

The estimator 130 estimates, from the usage information or the output 121, a voltage 131 that needs to be ideally output from the battery. An entropy calculator 140 calculates an information entropy 142 from a difference 141 between a voltage 131 estimated at the estimator 130 and a voltage 112 that is measured by a sensor 111 and that is collected by a battery information collector 110.

When the information entropy 142 is greater than a threshold 162, a battery abnormality determiner 160 determines that the battery is in the abnormal state. A notifier 170 notifies a user of an electronic apparatus of the abnormal state. For example, the notifier 170 transfers a warning signal to an external interface. The external interface warns a user of the abnormal state through a visual effect, an auditory effect, or a tactile effect, in response to the warning signal.

In an alternative embodiment, the entropy calculator 140 calculates the difference 141, instead of calculating the information entropy 142. In this example, when the difference 141 exceeds a threshold, the battery abnormality determiner 160 determines that the battery is in the abnormal state, which will be further described below.

Hereinafter, structural configurations and operations of a battery abnormality detection apparatus will be further described.

Figure 2:
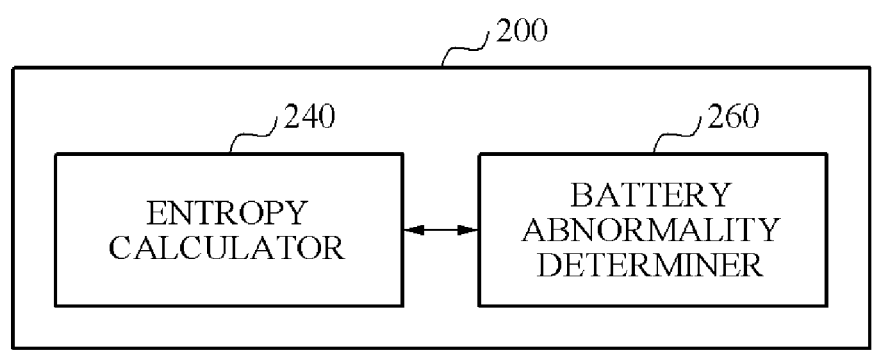
FIGS. 2 and 3 are block diagrams illustrating examples of an apparatus for detecting an abnormal state of a battery, in accordance with an embodiment.
Figure 3:
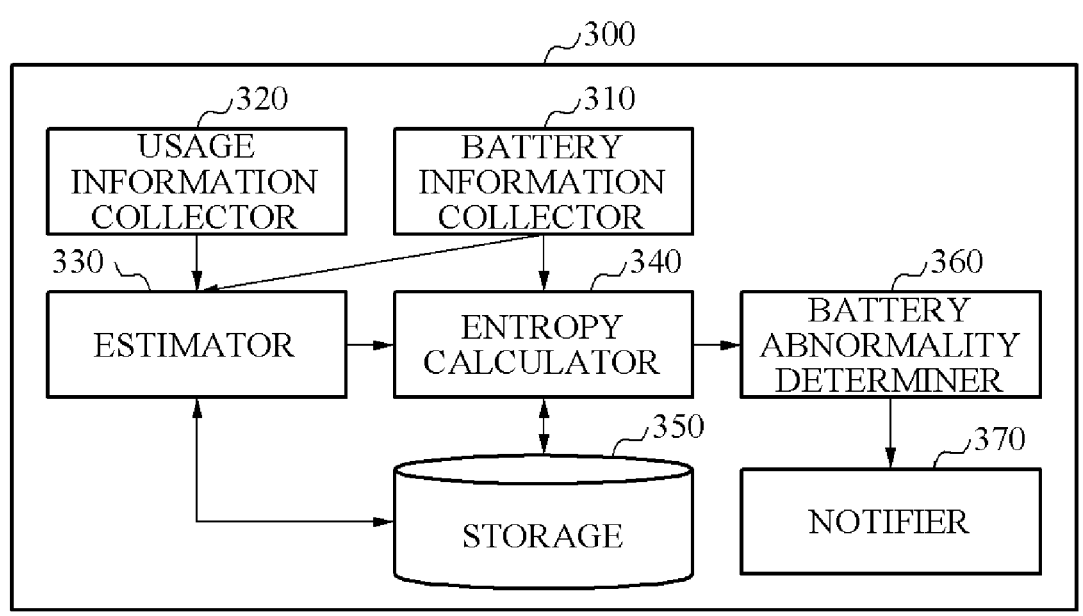

FIGS. 2 and 3 illustrate examples of a battery abnormality detection apparatus, in accordance with an embodiment.

Referring to FIG. 2, a battery abnormality detection apparatus 200 includes an entropy calculator 240 and a battery abnormality determiner 260.

The entropy calculator 240 calculates an information entropy from battery estimation information and battery measurement information. The battery estimation information corresponds to an output required to be output from a battery, and the battery measurement information is collected from the battery.

The battery abnormality determiner 260 determines whether the battery is in an abnormal state, based on the information entropy.

The battery abnormality detection apparatus 200 may be applicable, for example, to all electronic apparatuses employing battery cells, an electronic apparatus employing a battery module or a battery pack, and an electronic apparatus for managing a battery using a battery management system (BMS).

Hereinafter, a structure and corresponding operation of each of the entropy calculator 240 and the battery abnormality determiner 260 will be further described.

Referring to FIG. 3, a battery abnormality detection apparatus 300 includes a battery information collector 310, a usage information collector 320, an estimator 330, an entropy calculator 340, a storage 350, a battery abnormality determiner 360, and a notifier 370.

The battery information collector 310 collects battery measurement information from a battery. The battery measurement information includes, but it is not limited to, a measured voltage signal $V_o$, a measured current signal $I_o$, or a measured temperature signal $T_o$ of the battery. The battery information collector 310 transfers the battery measurement information directly or through the estimator 330 to the entropy calculator 340.

The usage information collector 320 collects usage information associated with a usage history of an electronic apparatus equipped with the battery. Additionally, the usage information collector 320 transforms the usage information to a power P corresponding to an output required to be output from the battery. For example, the usage information collector 320 collects, as the power P, a power calculated from the output and raw data corresponding to the usage information during a time window of a predetermined length, and transfers the collected power to the estimator 330. The time window is a temporal length of information set to compute an information entropy.

The estimator 330 acquires battery estimation information from the usage information. Additionally, the estimator 330 acquires estimated voltage $V_e$, based on the power P to which the usage information is transformed at the usage information collector 320. For example, the estimator 330 acquires, from the usage information, battery estimation information, or the estimated voltage $V_e$ to be output from the battery. The battery estimation information is information corresponding to an ideal output from the battery, not information actually measured from the battery, and includes, for example, the power P and the estimated voltage $V_e$.

The battery estimation information includes the power P and the estimated voltage $V_e$, however, there is no limitation thereto. For instance, the battery estimation information may be information of an estimated current, or an estimated temperature, that may be estimated from the usage information, and may include all information corresponding to a required or ideal output from the battery.

In an example, the estimator 330 receives the power P collected by the usage information collector 320, and the voltage signal $V_o$ collected at the battery information collector 310. The estimator 330 applies the received voltage signal $V_o$ to a current and an internal resistance of the battery, and acquires the estimated voltage $V_e$. The current and the internal resistance corresponds to the power P, that is, a power required to be output from the battery.

In another example, the estimator 330 calculates the estimated voltage $V_e$ by a voltage-current formula (for example, "P=VI" and "V=IR"). The estimator 330 determines a current I, based on the power P derived from the usage information collector 320 and the voltage signal $V_o$ acquired by the battery information collector 310. The estimator 330 derives a formula "$R=P/I^2$" from formulae "P=VI" and "V=IR," and acquires an internal resistance R of the battery corresponding to the power P transformed from the usage information. The estimator 330 acquires the estimated voltage $V_e$ based on the current I and the internal resistance R.

The estimated voltage $V_e$ is an accurate ideal voltage value corresponding to an output that an electronic apparatus equipped with a battery requires the battery to output.

In still another example, the estimator 330 converts the usage information to the power P, and calculates an estimated voltage $V_e$ corresponding to the power P. The estimator 330 calculates a power required by the electronic apparatus including the battery to perform a predetermined operation that may be included, for example, in a usage history of a user. For example, in an EV, a torque and an RPM are determined based on a degree to which an accelerator pedal is pressed for acceleration. In such example, the estimator 330 calculates a power required to be output from a battery, based on the torque and the RPM. The estimator 330 applies a simple power formula (for example, "P=VI") and Ohm's law (for example, V=IR) to the calculated power to calculate the estimated voltage $V_e$.

The estimator 330 transfers to the entropy calculator 340 the estimated voltage $V_e$ corresponding to the output required to be output from a battery. Additionally, the estimator 330 transfers to the entropy calculator 340 the battery measurement information collected at the battery information collector 310.

The entropy calculator 340 calculates an information entropy based on the battery estimation information from the estimator 330 and the battery measurement information. As previously described, the battery information collector 310 transfers the battery measurement information directly or through the estimator 330 to the entropy calculator 340. The calculated information entropy is transferred to the battery abnormality determiner 360. An example in which the entropy calculator 340 calculates an information entropy will be further described with reference to FIG. 8.

The storage 350 stores a difference between the battery estimation information and the battery measurement information. For example, the storage 350 stores a result of a comparison between the battery measurement information and the battery estimation information obtained during a time window of a predetermined length in which the entropy calculator 340 calculates an information entropy. The predetermined length is a temporal length of the time window, and is defined, for example, based on an operation processing capability of a battery abnormality detection apparatus and a calculation efficiency of an information entropy.

For example, when data is stored of a predetermined size (for example, a difference) to be used to calculate an information entropy at the entropy calculator 340, and when new data is input, the storage 350 deletes or overwrites pre-stored data or data stored for a longest period of time.

The battery abnormality determiner 360 determines based on the information entropy whether the battery is in the abnormal state.

The notifier 370 notifies a user of the electronic apparatus including the battery that a current state of the battery is the abnormal state, in response to the battery abnormality determiner 360 determining that the battery is in the abnormal state.

Figure 4:
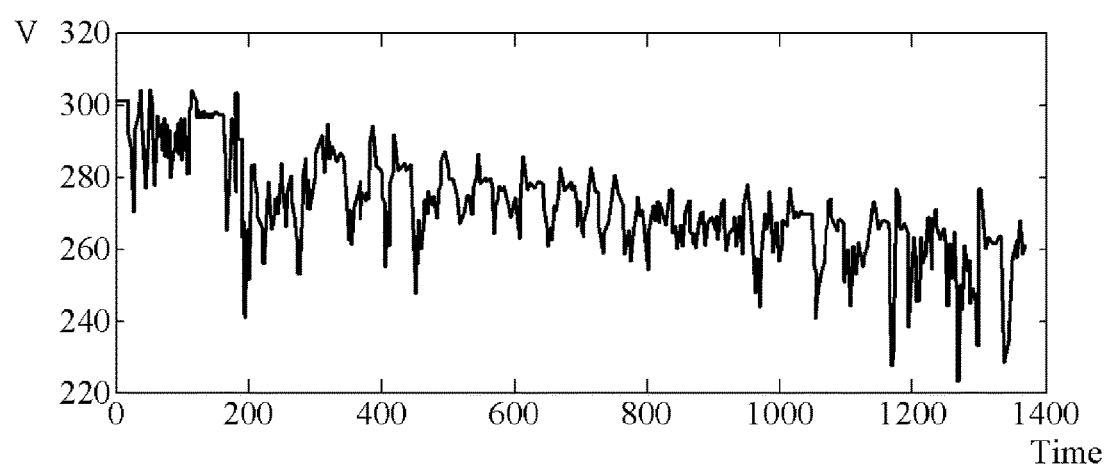
FIG. 4 is a graph illustrating an example of battery measurement information, in accordance with an embodiment.

FIG. 4 illustrates an example of battery measurement information, in accordance with an embodiment.

A battery information collector collects battery measurement information. The battery measurement information of FIG. 4 includes, for example, a voltage signal $V_o$ measured directly from a battery.

Figure 5:
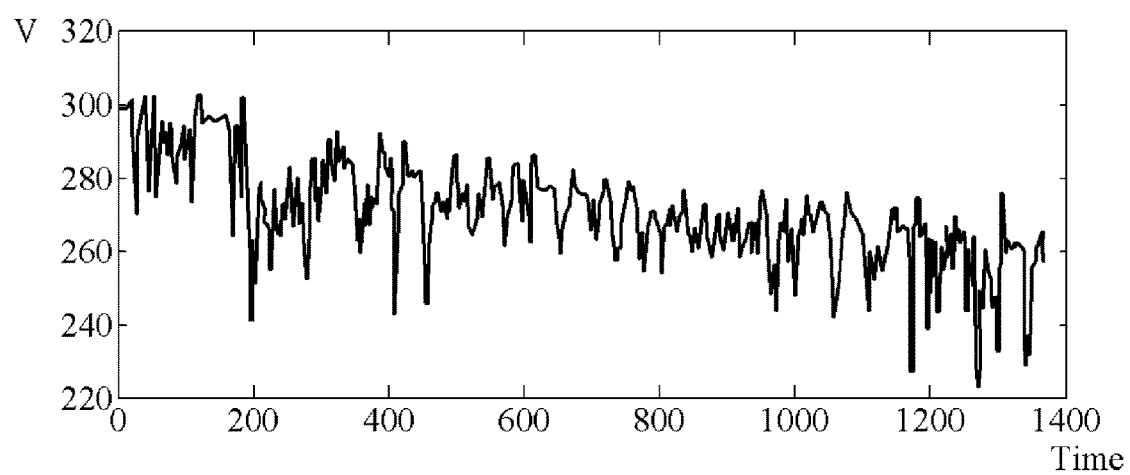
FIG. 5 is a graph illustrating an example of battery estimation information, in accordance with an embodiment.

FIG. 5 illustrates an example of battery estimation information, in accordance with an embodiment.

An estimator acquires battery estimation information from usage information. The battery estimation information of FIG. 5 includes, for example, an estimated voltage $V_e$ acquired indirectly from the usage information.

Figure 6:
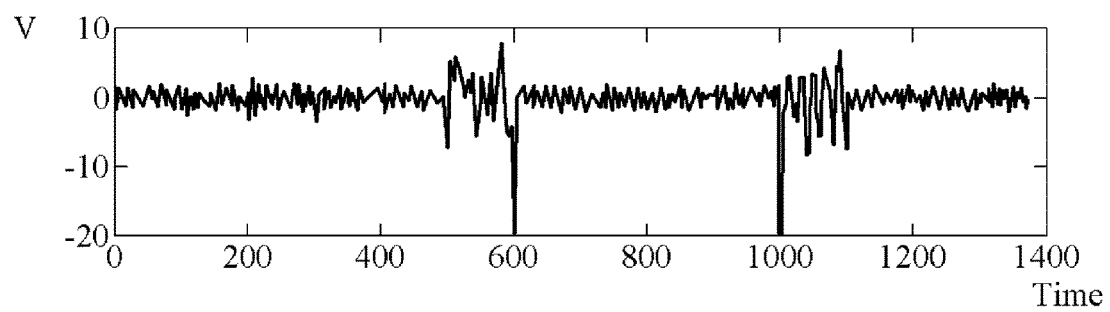
FIG. 6 is a graph illustrating an example of a difference between battery measurement information and battery estimation information, in accordance with an embodiment.

FIG. 6 illustrates an example of a difference between battery measurement information and battery estimation information, in accordance with an embodiment.

An entropy calculator may calculate a difference $\Delta V_t$ between battery measurement information and battery estimation information. The calculated difference $\Delta V_t$ is stored in a storage during a time window of a predetermined length. The calculated difference $\Delta V_t$ is, for example, a difference between the voltage signal $V_o$ of FIG. 4 and the estimated voltage $V_e$ of FIG. 5.

Figure 7:
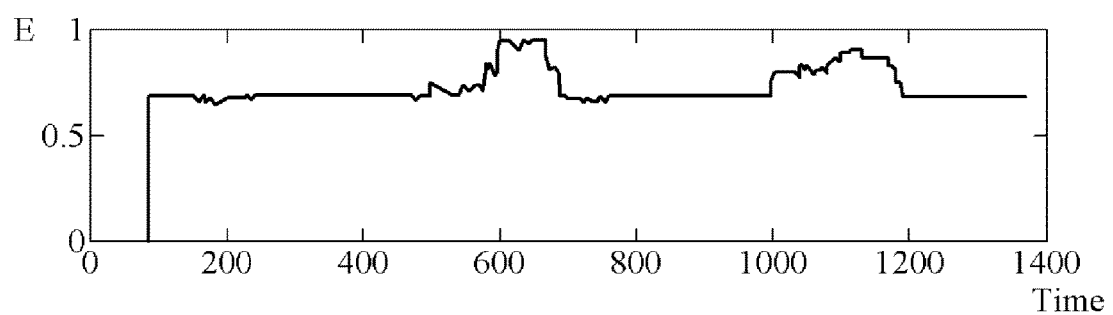
FIG. 7 is a graph illustrating an example of an information entropy calculated from battery measurement information and battery estimation information, in accordance with an embodiment.

FIG. 7 illustrates an example of an information entropy calculated from battery measurement information and battery estimation information, in accordance with an embodiment.

An entropy calculator calculates an information entropy based on a result of a comparison between battery measurement information and battery estimation information. For example, the entropy calculator calculates an information entropy based on a difference $\Delta V_t$ between battery measurement information and battery estimation information. An example of an operation of calculating an information entropy will be further described with reference to FIG. 8.

Figure 8:
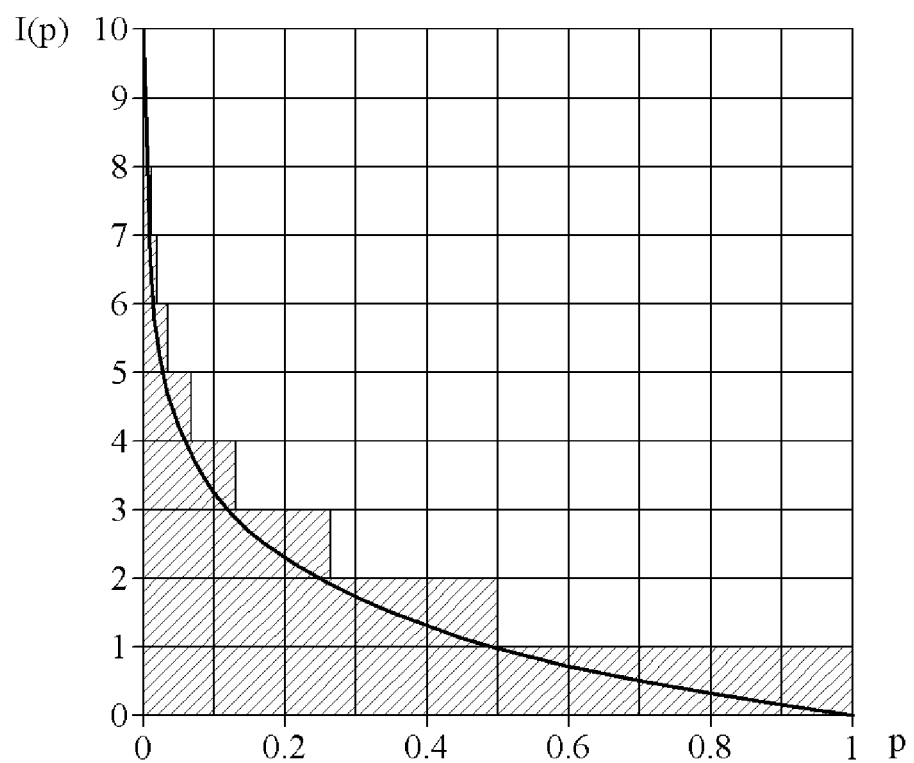
FIG. 8 is a graph illustrating an example of an information entropy corresponding to a probability that information is generated, in accordance with an embodiment.

FIG. 8 illustrates an example of an information entropy corresponding to a probability that information is generated, in accordance with an embodiment.

An information entropy is an amount of information included in a signal or an event based on an entropy concept. The information entropy corresponds to a measure of uncertainty in a random variable. In the information entropy, an amount of information with a high possibility of generation is reduced, and an amount of information with a low possibility of generation is increased.

In accordance with an illustrative configuration, an information entropy E is defined as shown in Equation 1 below.

$$\text{Entropy } E = -\Sigma p(x) \cdot \log(p(x)) \qquad \text{[Equation 1]}$$

In Equation 1, E denotes the information entropy, x denotes arbitrary data, and p(x) denotes a possibility that the arbitrary data x is generated (for example, a probability).

In an example, when the information entropy E has a value of "0" and a probability that the data x is generated has a value of "1," indicates that the data x is clearly generated. The information entropy E of "0" indicates that a value of information, that is, an amount of information is "0." In other words, the information entropy E of "0" indicates that uncertainty of the data x does not exist.

In another example, when the information entropy E has a value of "1" and a probability that the data x is generated may have a value of "0," indicates that the data x is not absolutely generated or is generated at an extremely low probability.

FIG. 8 illustrates an amount I(p) of information based on a possibility p of generation of information. The amount I(p) of information is measured in bits. Hereinafter, in accordance with an embodiment, a difference $\Delta V_t$ between an estimated voltage $V_e$ and a measured voltage signal $V_o$ is used as arbitrary data x.

An entropy calculator in a battery abnormality detection apparatus calculates an entropy of a difference $\Delta V_t$ between an estimated voltage $V_e$ and a measured voltage signal $V_o$, and the battery abnormality detection apparatus determines an abnormal state of the battery that will be described below.

In an example, a difference $\Delta V_t$ between an estimated voltage $V_e$ and a measured voltage signal $V_o$ indicates that a battery does not operate normally. The estimated voltage $V_e$ is a value of a voltage that needs to be ideally output from the battery based on a load applied to the battery during an operation of the battery. Theoretically, when a battery normally operates, the estimated voltage $V_e$ may need to be equal to the measured voltage signal $V_o$, and, therefore, the difference $\Delta V_t$ may be "0." When a value of the measured voltage signal $V_o$ is different from a value of the estimated voltage $V_e$, a phenomenon other than a theoretical phenomenon of the battery may occur.

In another example, the information entropy is used to easily determine whether a difference $\Delta V_t$ between two voltages, for example, an estimated voltage $V_e$ and a voltage signal $V_o$, has a frequent value or an infrequent value.

As shown in FIG. 8, when a difference $\Delta V_t$ between an estimated voltage $V_e$ and a measured voltage signal $V_o$ needs to have a value of "0" and the battery normally operates at all times, a probability that the difference $\Delta V_t$ is "0" may be "1." Accordingly, the information entropy has a value of "0" at all times. In another example, when the difference $\Delta V_t$ has a value of "v" other than "0," the information entropy E has a value close to "1" due to a low probability that the value of "v" is generated. Accordingly, the difference $\Delta V_t$ of "v" indicates extremely uncertain information of the battery, thereby defining an abnormal state of the battery. Furthermore, when the value of "v" indicates a state of the battery immediately before an extreme explosion of the battery or a reduction in a life of the battery due to an overload, all information entropies have values close to "1."

To secure stability of the battery, a determination of whether the battery is in an abnormal state needs to be quickly and accurately made. Accordingly, in accordance with an embodiment, an apparatus and corresponding method to detect an abnormal state of a battery based on an information entropy to detect all of the above abnormal phenomena are provided as described above with reference, at least to FIGS. 1-3 and 8 and FIGS. 9 and 10 described below.

Figure 9:
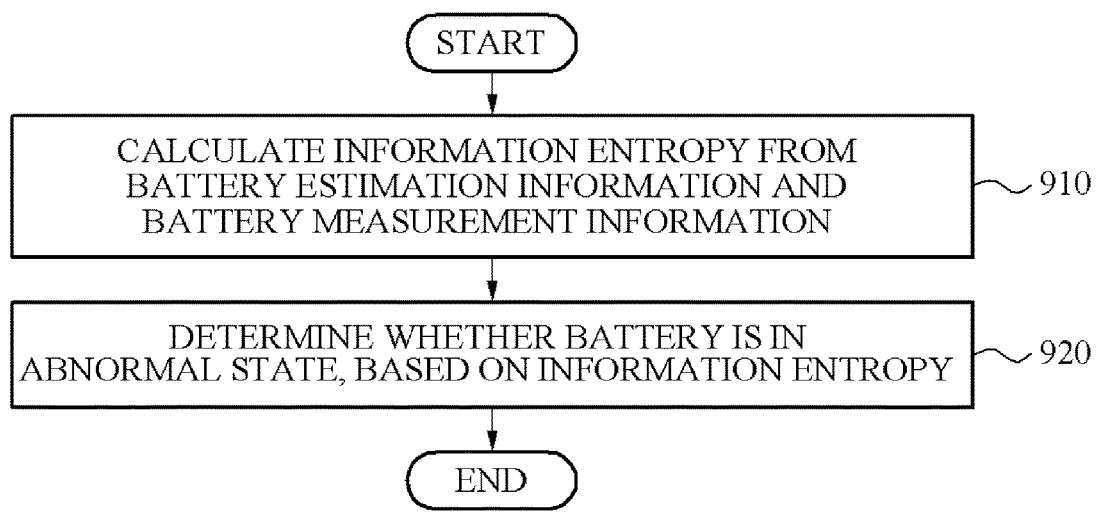
FIGS. 9 and 10 are flowcharts illustrating examples of a method of detecting an abnormal state of a battery, in accordance with an embodiment.
Figure 10:
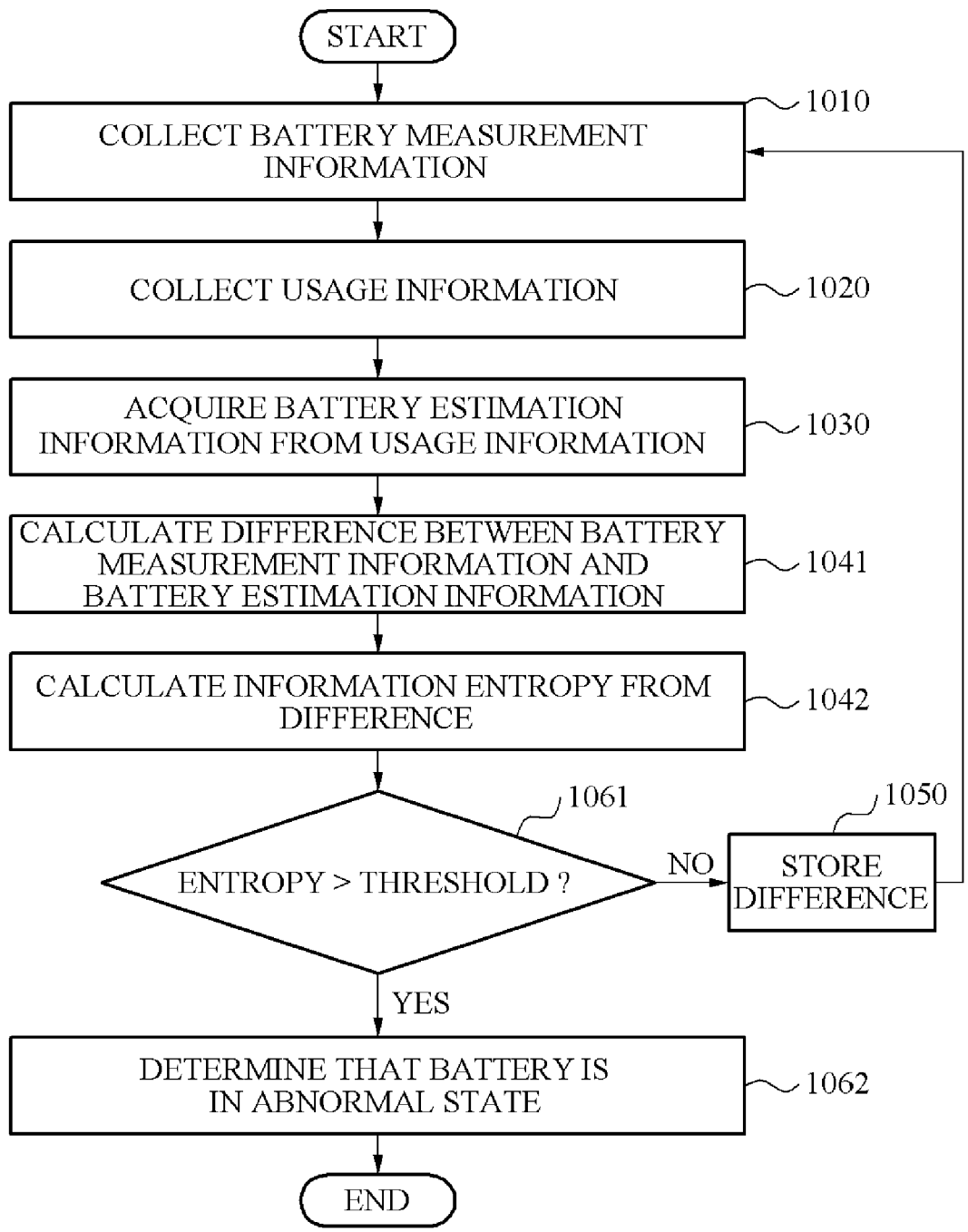

FIGS. 9 and 10 illustrate examples of a method to detect an abnormal state of a battery, in accordance with an embodiment.

FIG. 9 schematically illustrates an example of a method to detect an abnormal state of a battery.

Referring to FIG. 9, in operation 910, the method, using an entropy calculator, calculates an information entropy from battery estimation information and battery measurement information. The battery estimation information includes, for example, information that is estimated indirectly from usage information and that is associated with a power, P, corresponding to an output required to be ideally output from the battery. The usage information is associated with a usage history of an electronic apparatus. Additionally, the battery measurement information includes, for example, information that is associated with a power of the battery measured directly from the battery. The information entropy is calculated as described above with reference to FIG. 8.

In operation 920, based on the information entropy, the method at a battery abnormality determiner determines whether the battery is in the abnormal state. For example, the battery abnormality determiner compares the information entropy to a threshold, and determines whether the battery is in the abnormal state.

FIG. 10 illustrates another example of the method of detecting an abnormal state of a battery, in accordance with an embodiment.

Referring to FIG. 10, in operation 1010, the method at a battery information collector collects battery measurement information. For example, the method at the battery information collector collects, using a sensor, battery measurement information. The battery measurement information is all information measured in the battery, and includes, for example, a voltage signal, a current signal, or a temperature signal.

In operation 1020, the method at a usage information collector collects usage information. For example, the usage information collector collects usage information associated with a usage history of the electronic apparatus including the battery. The usage history includes a history indicating that the electronic apparatus is operated by a user, and the usage information is information about the use of the battery in the electronic apparatus, and includes load information about a load applied to the battery.

In operation 1030, the method, using an estimator, acquires battery estimation information from the usage information. For example, the estimator transforms the usage information to a power P corresponding to the output, and calculates an estimated voltage $V_e$ corresponding to the power P. The estimator extracts battery estimation information from an electrical model of the battery that is constructed in advance. The electrical model is constructed, for example, based on an urban dynamometer driving schedule (UDDS) profile.

In operation 1041, the method, using an entropy calculator, calculates a difference between the battery measurement information and the battery estimation information. The calculated difference is stored during a time window of a predetermined length.

In operation 1042, the method, using the entropy calculator, calculates an information entropy from the difference. For example, the entropy calculator calculates an information entropy based on Equation 1 described above. The entropy calculator calculates a probability that the difference occurs, and calculates the information entropy from the probability. The probability that the difference occurs is calculated, for example, based on a frequency that an arbitrary difference occurs within a time window of a predetermined length. For example, when a length of a time window is set to "n," and when an arbitrary difference occurs "m" times for the time window, a probability that the arbitrary difference occurs is represented by "m/n."

In operation 1061, the method uses a battery abnormality determiner to compare the information entropy to a threshold. For example, the method at the battery abnormality determiner determines whether a value of the information entropy calculated based on Equation 1 is greater than a threshold set in advance. The threshold is set, for example, by a user, a simulation, and an experiment.

In operation 1062, the method the battery abnormality determiner determines that the battery is in the abnormal state, in response to the value of the information entropy being greater than the threshold. In an example, when an interval, in which the value of the information entropy is greater than the threshold, is detected to be equal to or greater than a predetermined interval, the method determines that the battery is in the abnormal state. In another example, when an interval, in which the value of the information entropy is greater than the threshold, is detected at least a predetermined number of times, the method determines that the battery is in the abnormal state.

In operation 1050, the method stores in a storage the difference, in response to the value of the information entropy being equal to or less than the threshold. The method stores the difference in a time window of a predetermined length. Additionally, the method provides the entropy calculator with the stored difference. Operation 1050 may be performed as shown in FIG. 10, however, there is no limitation thereto. Accordingly, operation 1050 may be performed at a predetermined point in time after operation 1041.

In still another example of the method of detecting an abnormal state of a battery, the abnormal state of the battery is determined, based on a difference between battery measurement information and battery estimation information, without a need to calculate an information entropy.

For example, a battery information collector collects battery measurement information from a battery. An estimator acquires battery estimation information from an output from the battery. A battery abnormality determiner compares the battery measurement information and the battery estimation information, and determines whether the battery is in an abnormal state.

In this example, the estimator includes a usage information collector, and an entropy calculator. The usage information collector collects usage information associated with a usage history of an electronic apparatus equipped with the battery. The entropy calculator transforms the usage information to a power corresponding to the output, and calculates a voltage corresponding to the power.

When a difference between the battery measurement information and the battery estimation information is greater than a threshold, the battery abnormality determiner determines that the battery is in the abnormal state. The threshold is set, for example, by a user, a simulation, or an experiment.

According to various examples, a battery abnormality detection apparatus continues to detect an abnormal state of a battery, and may protect the battery and an electronic apparatus, despite an electric circuit not being blocked.

Additionally, before an occurrence of an abnormal phenomenon allowing the battery to be unavailable, the battery abnormality detection apparatus detects the abnormal state and warns the user of the electronic apparatus of the occurrence. Thus, it is possible to ensure a stable use of the battery for a relatively long period of time.

The battery abnormality detection apparatus accurately detects the abnormal state of the battery using the usage information of the electronic apparatus.

A usage history of the electronic apparatus, and usage information of the battery have an influence on all indices representing a state of the battery (for example, an output, a voltage, a current, a capacity, or a life of the battery). For example, when a high output is required to be output from the battery, a high current may be applied, which may cause a voltage drop. Indices representing the state of the battery include information representing a pure state of the battery and information on a state of the battery caused by the usage history. Accordingly, when state information associated with the usage history is not eliminated from the data collected from the battery, it may be difficult to determine a current state of the battery to be caused due to the use of the battery or abnormality of the battery.

The usage history of the electronic apparatus and the usage information of the battery are eliminated from a result value based on a difference between a measured voltage and an estimated voltage signal. Accordingly, despite the battery being used, the battery abnormality detection apparatus accurately detects the abnormal state of the battery, and effectively determines the abnormal state by expressing the difference by an information entropy.

In addition, the battery abnormality detection apparatus has a low calculation complexity. For example, the estimated voltage and the information entropy are calculated through a simple equation and; accordingly, the battery abnormality detection apparatus is effectively implemented in low-specification hardware. Furthermore, the battery abnormality detection apparatus detects, in real time, the abnormal state of the battery.

Furthermore, the battery abnormality detection apparatus is robust against noise. Despite an error in data collected at all times by the battery abnormality detection apparatus, the data is not affected by noise occurring in an extremely short moment (for example, an error in a sensor, and the like), by calculating an information entropy of data during a predetermined interval. The battery abnormality detection apparatus has a low malfunction possibility, because the battery abnormality detection apparatus is insensitive to noise.

The battery abnormality detection apparatus estimates a pure abnormal state of the battery by eliminating information on the usage information of the battery, and calculates, in real time, an information entropy due to a low calculation complexity for the information entropy. Additionally, the battery abnormality detection apparatus is robust against noise and; thus, it is possible to detect the abnormal state of the battery with a high accuracy.

The battery abnormality detection apparatus primarily detects the abnormal state of the battery in the electronic apparatus. For example, using the battery abnormality detection apparatus, an apparatus to detect the abnormal state at a plurality of layers may be constructed. The battery abnormality detection apparatus detects all abnormal states. When the abnormal state is primarily detected, the battery abnormality detection apparatus may secondarily inspect in detail hardware in an inspection station. For example, when the battery abnormality detection apparatus is applied to an EV and a battery inspection lamp is powered on, a user may visit a garage and the EV may be inspected in detail.

The units, estimators, determiners, notifiers, and collectors described herein may be implemented using hardware components. For example, the hardware components may include controllers, generators, processors, calculators, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

It is to be understood that in the embodiment of the present invention, the operations in FIG. 10 are performed in the sequence and manner as shown although the order of some operations and the like may be changed without departing from the spirit and scope of the described configurations. In accordance with an illustrative example, a computer program embodied on a non-transitory computer-readable medium may also be provided, encoding instructions to perform at least the method described in FIG. 10.

Program instructions to perform a method described in FIG. 10, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein may be easily construed by programmers skilled in the art to which the embodiments pertain based on and using the flow diagrams and block diagrams of the figures and their corresponding descriptions as provided herein.

The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

As a non-exhaustive illustration only, an electronic apparatus, a terminal or device described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus to detect an abnormal state of a battery, the apparatus comprising:
    a battery of an electronic device;
    one or more hardware processors comprising:
    an entropy calculator configured to calculate an information entropy based on battery estimation information and battery measurement information, wherein the battery estimation information corresponds to a theoretical output required from the battery based on a usage history of the battery, and the battery measurement information is collected from the battery;
    a battery abnormality determiner configured to determine whether the battery is in the abnormal state based on the information entropy, wherein the entropy calculator is configured to calculate a difference between the battery estimation information and the battery measurement information, to calculate a probability that the difference occurs, and to calculate the information entropy from the probability; and
    a protection device configured to disconnect the battery from the electronic device based on the information entropy, before an occurrence of an abnormality, in response to the battery being determined to be in the abnormal state.

2. The apparatus of claim 1, further comprising:
    a battery information collector configured to collect the battery measurement information;
    a usage information collector configured to collect usage information of a usage history of an electronic apparatus including the battery; and
    an estimator configured to acquire the battery estimation information from the usage information.

3. The apparatus of claim 2, wherein the estimator is configured to transform the usage information to a power corresponding to the output, and to calculate a voltage corresponding to the power.

4. The apparatus of claim 1, further comprising:
    an estimator configured to extract the battery estimation information from an electrical model of the battery.

5. The apparatus of claim 1, further comprising:
    a storage configured to store a result of a comparison between the battery estimation information and the battery measurement information during a time window of a predetermined length.

6. The apparatus of claim 1, wherein the entropy calculator is configured to calculate the information entropy based on a result of a comparison between the battery estimation information and the battery measurement information.

7. The apparatus of claim 1, wherein the battery abnormality determiner is configured to determine that the battery is in the abnormal state in response to a value of the information entropy being greater than a threshold.

8. The apparatus of claim 1, wherein the battery abnormality determiner is configured to determine that the battery is in the abnormal state in response to an interval, in which a value of the information entropy is greater than a threshold value of the information entropy, being detected to be equal to or longer than a predetermined interval.

9. The apparatus of claim 1, wherein the usage history comprises an intensity measured when a user presses an accelerator pedal, a time period during which the accelerator pedal is pressed, an amount of pressure measured when the user presses a brake pedal, a time duration in which the brake pedal is pressed.

10. The apparatus of claim 1, further comprising a notifier that warns a user of the abnormal state through a visual effect, an auditory effect, or a tactile effect.

11. A method to detect an abnormal state of a battery of an electronic device, the method comprising:
    calculating, using one or more hardware processors, an information entropy based on battery estimation information and battery measurement information, wherein the battery estimation information corresponds to a theoretical output required by the battery based on a usage history of the battery, and the battery measurement information is collected from the battery; and
    determining, using the one or more hardware processors, whether the battery is in the abnormal state based on the information entropy, wherein the calculating comprises:
    calculating a difference between the battery estimation information and the battery measurement information;
    calculating a probability of the difference from occurring;
    calculating the information entropy from the probability; and
    disconnecting the battery from the electronic device, based on the information entropy, before an occurrence of an abnormality, using a protection device, in response to the battery being determined to be in the abnormal state.

12. The method of claim 11, further comprising:
collecting the battery measurement information from the battery;
collecting usage information associated with a usage history of an electronic apparatus including the battery; and
estimating the battery estimation information from the usage information.

13. The method of claim 12, wherein the estimating comprises transforming the usage information to a power corresponding to the output and calculating a voltage corresponding to the power.

14. The method of claim 11, wherein the calculating comprises storing a result of a comparison between the battery estimation information and the battery measurement information during a time window of a predetermined length to calculate the information entropy.

15. The method of claim 11, wherein the calculating comprises calculating the information entropy based on a result of a comparison between the battery estimation information and the battery measurement information.

16. The method of claim 11, wherein the determining comprises determining that the battery is in the abnormal state in response to a value of the information entropy being greater than a threshold.

17. A non-transitory computer readable recording medium storing a program to cause a computer to implement the method of claim 11.

18. A method to detect an abnormal state of a battery of an electronic device, the method comprising:
collecting, using one or more hardware processors, battery measurement information from the battery;
acquiring, using one or more hardware processors, battery estimation information based on a usage history of the battery, wherein the battery estimation information indicates a theoretical output required by the battery; and
comparing, using one or more hardware processors, the battery measurement information and the battery estimation information, calculating a probability that a difference between the battery measurement information and the battery estimation information occurs, to determine whether the battery is in an abnormal state;
determining that the battery is in the abnormal state in response to a difference between the battery estimation information and the battery measurement information being greater than a threshold; and
disconnecting the battery from the electronic device, before an occurrence of an abnormality, using a protection device, in response to the battery being determined to be in the abnormal state.

19. The method of claim 18, wherein the acquiring comprises:
collecting usage information associated with a usage history of an electronic apparatus including the battery; and
transforming the usage information to a power corresponding to the output and calculating a voltage corresponding to the power, wherein the battery estimation information comprises at least one of a power corresponding to the theoretical output and a voltage corresponding to the power.

20. A battery abnormality detection apparatus, comprising:
a battery of an electronic device;
one or more hardware processors comprising:
a battery information collector configured to collect battery measurement information from a battery;
a usage information collector configured to collect usage information associated with a usage history of an electronic apparatus including the battery and transform the usage information to a power corresponding to an output required from the battery;
an estimator configured to acquire battery estimation information from the usage information indicating a theoretical output of the battery, or from an estimated voltage based on the power;
an entropy calculator configured to calculate an information entropy based on the battery estimation information and the battery measurement information;
a battery abnormality determiner configured to determine, based on the information entropy, whether the battery is in the abnormal state; and
a protection device configured to disconnect the battery from the electronic device, based on the information entropy, before an occurrence of an abnormality, in response to the battery being determined to be in the abnormal state,
wherein the entropy calculator is configured to calculate a difference between the battery estimation information and the battery measurement information, to calculate a probability that the difference occurs, and to calculate the information entropy from the probability.

21. The apparatus of claim 20, further comprising:
a storage configured to store a difference between the battery estimation information and the battery measurement information during a time window of a predetermined length in which the entropy calculator calculates the information entropy; and
a notifier configured to notify a current state of the battery as the abnormal state, in response to the battery abnormality determiner determining that the battery is in the abnormal state.

22. The apparatus of claim 20, wherein the battery measurement information comprises at least one of a measured voltage signal, a measured current signal, and a measured temperature signal of the battery.

23. The apparatus of claim 20, wherein the power is calculated from the output and raw data corresponding to the usage information during a time window of a predetermined length, and the time window is a temporal length of information set to compute the information entropy.

24. The apparatus of claim 20, wherein the battery estimation information comprises the power and the estimated voltage, an estimated current, or an estimated temperature estimated from the usage information, and information corresponding to a required output from the battery.

25. The apparatus of claim 20, wherein the estimator is further configured to receive the power, receive a voltage signal collected at the battery information collector, and apply the received voltage signal to a current and an internal resistance of the battery to acquire the estimated voltage.

* * * * *